United States Patent [19]

Vyas et al.

[11] Patent Number: 4,885,314

[45] Date of Patent: Dec. 5, 1989

[54] NOVEL HMG-COA REDUCTASE INHIBITORS

[75] Inventors: Kamlesh P. Vyas, Harleysville; Hanumath P. Kari, Hatfield, both of Pa.

[73] Assignee: Merck & Co., Inc., Rahway, N.J.

[21] Appl. No.: 239,238

[22] Filed: Sep. 1, 1988

Related U.S. Application Data

[62] Division of Ser. No. 67,503, Jun. 29, 1987, Pat. No. 4,782,084.

[51] Int. Cl.$^4$ ............................................. A61K 31/19
[52] U.S. Cl. ..................................... 514/630; 514/653; 514/766; 514/824; 560/56; 560/119; 562/466; 564/222; 564/344
[58] Field of Search ................. 562/466; 514/630, 653, 514/824, 766; 560/56, 119; 564/222, 344

[56] References Cited

U.S. PATENT DOCUMENTS 4,319,039  3/1982  Albers-Schonberg ............... 514/824

FOREIGN PATENT DOCUMENTS 0033537  8/1981  European Pat. Off. ............ 514/824

*Primary Examiner*—Glennon H. Hollrah
*Assistant Examiner*—Amelia A. Owens
*Attorney, Agent, or Firm*—Melvin Winokur; Joseph F. DiPrima

[57] ABSTRACT

Novel 3-hydroxy-3-methylglutaryl-coenzyme A (HMG-CoA) reductase inhibitors which are useful as antihypercholesterolemic agents and are represented by the following general structural formulae (I) or (II):

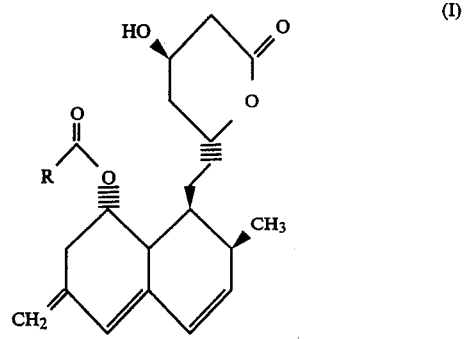

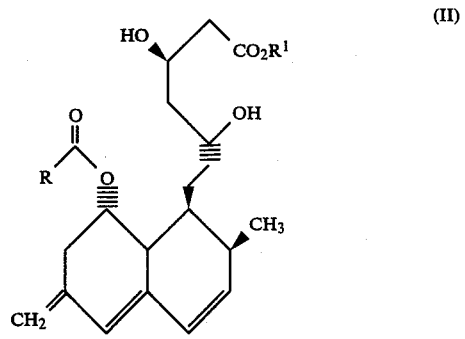

and pharmaceutically acceptable salts thereof the compounds of the formula (II) in which $R^1$ is hydrogen are disclosed.

6 Claims, No Drawings

NOVEL HMG-COA REDUCTASE INHIBITORS

This is a division of application Ser. No. 067,503, filed 6/29/87, now U.S. Pat. No. 4,782,084.

BACKGROUND OF THE INVENTION

Hypercholesterolemia is known to be one of the prime risk factors of cardiovascular disease, such as arteriosclerosis, and there is still no effective antihypercholesterolemic agent commercially available that has found wide patient acceptance. The bile acid sequestrants seem to be moderately effective but they must be consumed in large quantities, i.e. several grams at a time and they are not very palatable.

There are agents known, however, that are very active antihypercholesterolemic agents that function by limiting cholesterol biosynthesis by inhibiting the enzyme, HMG-CoA reductase. These agents include the natural fermentation products compactin and mevinolin and a variety of semisynthetic and totally synthetic analogs thereof. The naturally occurring compounds and their semisynthetic analogs have the following general structural formulae:

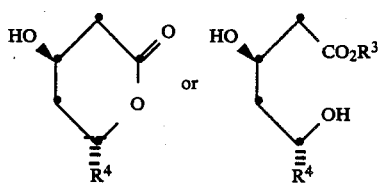

wherein:

$R^3$ is hydrogen, $C_{1-5}$ alkyl or $C_{1-5}$ alkyl substituted with a member of the group consisting of phenyl, dimethylamino, or acetylamino;

$R^4$ is:

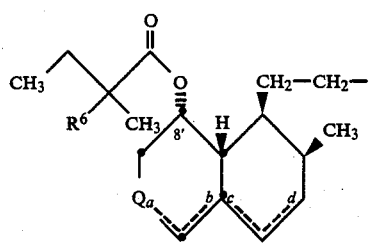

wherein Q is

or

$R^5$ is H or OH;

$R^6$ is hydrogen or methyl; and a, b, c, and d represent optional double bonds, especially where b and d represent double bonds or a, b, c, and d are all single bonds.

Active metabolites of mevinolin which possess a 2,3,5,6,7,8-hexahydronapthyl moiety and a 3-hydroxy group are disclosed and claimed in co-pending application Ser. No. 856,251, filed Apr. 28, 1986. These metabolites are represented by the following general structure formulae:

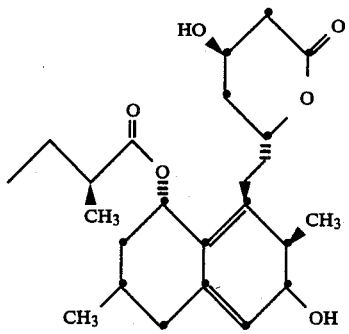

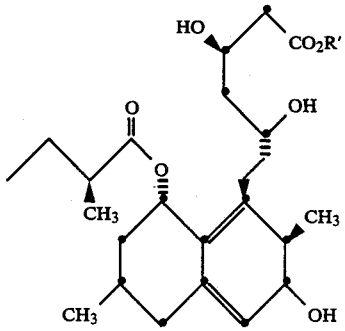

SUMMARY OF THE INVENTION

This invention relates to novel compounds which are HMG-CoA reductase inhibitors and are useful as antihypercholesterolemic agents. Specifically, the compounds of this invention are metabolites of mevinolin and related compounds which possess a 1,2,7,8,8a-pentahydronapthyl moiety and a 6-exomethylene group. Additionally, pharmaceutical compositions of these novel compounds, as a sole therapeutically active ingredient, and in combination with bile acid sequestrants are disclosed.

DETAILED DESCRIPTION OF THE INVENTION

The specific HMG-CoA reductase inhibitors of this invention are the compounds represented by the following general structural formulae (I) and (II):

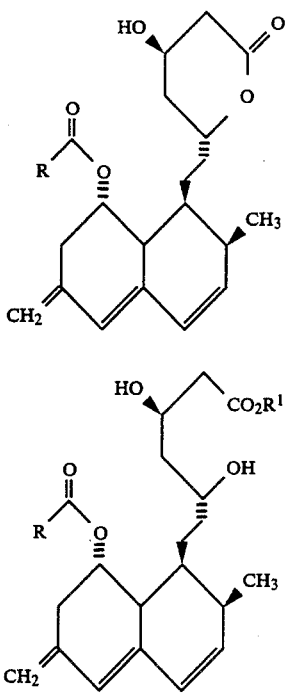

wherein:

R is $C_{1-10}$ alkyl;

$R^1$ is hydrogen, $C_{1-5}$ alkyl, $C_{1-5}$ alkyl substituted with a member of the group consisting of phenyl, dimethylamino, or acetylamino and pharmaceutically acceptable salts of the compound (II) in which $R^1$ is hydrogen.

One embodiment of this invention are the compounds of the formulae (I) and (II) wherein R is sec-butyl or 1,1-dimethylpropyl and $R^1$ is hydrogen.

Illustrative of this embodiment is 6(R)-[2-[8(S)-(2-methylbutyryloxy)-2(S)-methyl-6-exomethylene-1,2,7,8,8a-pentahydronaphthyl-1-]ethyl]-4(R)-hydroxy-3,4,5,6-tetrahydro-2H-pyran-2-one.

Another embodiment of this invention is the class of compounds of the formula (II) wherein $R^1$ is $C_{1-5}$ alkyl and pharmaceutically acceptable salts of the compounds of the formula (II) wherein $R^1$ is hydrogen.

The pharmaceutically acceptable salts of this invention include those formed from cations such as sodium, potassium, aluminum, calcium, lithium, magnesium, zinc, and from bases such as ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

The compound of the formula (I) is conveniently prepared from mevinolin by the incubation with rat liver microsomes.

The compounds of the formula (II) wherein $R^1$ is hydrogen or a pharmaceutically acceptable salt thereof are readily prepared by the mild basic hydrolysis of the lactone moiety of the compounds of formula (I), careful acidification and formation of the appropriate salt utilizing standard procedures.

The compounds of the formula (II) wherein R is $C_{1-5}$ alkyl or a substituted $C_{1-5}$ alkyl may be conveniently prepared by the procedures described in U.S. Pat. No. 4,342,767.

The compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 2 mg to 2000 mg (preferably 10 to 100 mg) which may be given in two to four divided doses. Higher doses may be favorably employed as required.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)iminotrimethylene dihalide]. The relative amounts of the compounds of this invention and these polymer is between 1:100 and 1:15,000.

The intrinsic HMG-CoA reductase inhibition activity of the claimed compounds is measured in the in vitro protocol described is *J. Med. Chem.*, 1985, 28, page 347.

The compound of the formula (II) wherein R is sec butyl and $R^1$ is hydrogen as the potassium salt exhibited a relative inhibitory activity of 50 percent of that exhibited by mevinolin as measured by the above reference protocol.

Included within the scope of this invention is the method of treating arteriosclerosis, famial hypercholesterolemia or hyperlipidemia which comprises administering to a subject in need of such treatment a nontoxic therapeutically effective amount of the compounds of formulae (I) or (II) or pharmaceutical compositions thereof.

The following examples illustrate the preparation of the compounds of the formulae (I) and (II) and their incorporation into pharmaceutical compositions and as such are not to be considered as limiting the invention set forth in the claims appended hereto.

EXAMPLE 1

Preparation of 6(R)-[2-[8(S)-(2-methylbutyryloxy)-2(S)-methyl-6-exomethylene-1,2,7,8,8a-pentahydronaphthyl-1-]ethyl]-4(R)-hydroxy-3,4,5,6-tetrahydro-2H-pyran-2-one 1. Preparation of Liver Microsomes:

Liver microsomes were prepared from control male CRCD rats (180–200 g) and control male CF-1 mice (25 g) according to the method of Lu and Levin [Biochem. Biophys. Res. Commun. 46: 1334–1339 (1972)]. Microsomal protein concentrations were measured by the Biuret method using bovine serum albumin as standard.

2. Incubations:

Large-scale incubations were performed to isolate sufficient quantity of metabolites for structure elucidation. Large-scale incubations were carried out in a 25 ml erlenmeyer flask and consisted of 1 mmole potassium phosphate buffer (pH 7.4), 30 μmole $MgCl_2$, 5 μmole triphosphopyridine nucleotide sodium salt (NADPH), 20 mg microsomal protein from either rat or mouse and 1 μmole [1-$C^{14}$-2-methylbutanoate]mevinolin (with a specific activity of 0.8μ Ci/mg) (dissolved in 200 μl acetone) in a final volume of 10 ml. Sixteen flasks were incubated at 37° C. for 30 minutes. At the end of the incubation period the reaction was terminated by adding 10 ml acetone, and unreacted substrate and metabolites were extracted using 20 ml ethyl acetate. After centrifugation, the organic layer was carefully removed, pooled, dried over anhydrous sodium sulfate, filtered over glass wool and concentrated in vacuo to dryness. Concentrated extracts were stored at −20° C. prior to isolation of metabolites by HPLC.

3. Isolation:

Concentrated pooled extract from large scale incubations was reconstituted in 2.5 ml n-propanol and metabolites were isolated using a Waters μBondapak ODS column (1×30 cm) eluted with a linear gradient (2%/min) of 30% to 90% acetonitrile in water at a flow rate of 3.0 ml/min. The eluate was monitored at 238 nm and metabolite fractions were collected over ice. The fraction containing the desired product (Rt-23.6 min) was concentrated to a small volume (∼0.5 ml) in vacuo at 30° C. The resulting cloudy solution was clarified by mixing with 0.5 ml acetonitrile and the metabolite was repurified by HPLC as described above, except that a linear gradient (1%/min) of 50% to 70% acetonitrile in water was used. The eluate was monitored at 274 nm. The eluate was concentrated to ∼10 ml in vacuo at 30° C. and the metabolite was extracted into ethylacetate (2×6 ml). After centrifugation, the organic layer was carefully removed, dried over anhydrous sodium sulfate, filtered and evaporated gently under a stream of $N_2$. The metabolite was further dried overnight in a dessicator over phosphorus pentoxide at −70° C.

Mass spectrometry and nuclear magnetic resonance spectroscopy confirm the structure.

NMR (acetonitrile-$d_6$) 4.92 and 4.79 ppm: (assigned to 6-exomethylene protons) and 6.05 ppm (5H, assigned olefinic protons) The position of the 6-exomethylene protons was further confirmed by difference NOE experiments. Characteristic mevinolin 6-methyl proton resonance at 1.1 ppm was absent.

EXAMPLES 2 TO 5

Utilizing the general procedure of Example 1, but substituting an equimolar amount of the appropriately 8-acyloxy substituted analog for mevinolin, the following compounds of the formula (I) are prepared:

| Compound No. | R |
|---|---|
| 2 | 1,1-dimethylpropyl |
| 3 | n-hexyl |
| 4 | 1,1-dimethylethyl |

EXAMPLE 6

As a specific embodiment of a composition of this invention, 20 mg of the compound of Example 1 is formulated with sufficient finely divided lactose to provide a total amount of 580 to 590 mg to fill a size 0 hard gelatin capsule.

What is claimed is:

1. A compound represented by the following general structural formula (II):

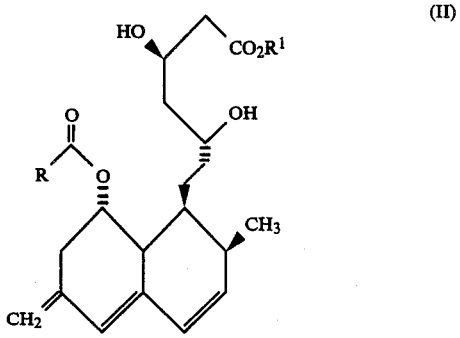

wherein:

R is $C_{1-10}$ alkyl; and $R^1$ is hydrogen, $C_{1-5}$ alkyl or $C_{1-5}$ alkyl substituted with a member of the group consisting of phenyl, dimethylamino or acetylamino or a pharmaceutically acceptable salt of the compound (II) in which $R^1$ is hydrogen.

2. A compound of claim 1 wherein R is sec-butyl or 1,1-dimethylpropyl.

3. A hypocholesterolemic, hypolipidemic pharmaceutical composition comprising a nontoxic therapeutically effective amount of a compound of claim 1 and a pharmaceutically acceptable carrier.

4. A method of inhibiting cholesterol biosynthesis comprising the administration to a subject in need of such treatment a nontoxic therapeutically effective amount of a compound of claim 1.

5. A compound of claim 1 wherein R is sec-butyl and $R^1$ is H and a pharmaceutically acceptable salt thereof.

6. A composition of claim 3 wherein the therapeutically active ingredient $R^1$ is sec-butyl and R is H and a pharmaceutically acceptable salt thereof.

* * * * *